United States Patent
McLean (10) Patent No.: US 8,029,571 B2
(45) Date of Patent: *Oct. 4, 2011

(54) CONTAINMENT SYSTEM FOR CONSTRAINING A PROSTHETIC COMPONENT

(75) Inventor: Terry W. McLean, Cordova, TN (US)

(73) Assignee: Smith & Nephew, Inc., Cordova, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/790,023

(22) Filed: May 28, 2010

(65) Prior Publication Data

US 2010/0234963 A1     Sep. 16, 2010

Related U.S. Application Data

(63) Continuation of application No. 12/026,088, filed on Feb. 5, 2008, now Pat. No. 7,749,277, which is a continuation of application No. 10/755,701, filed on Jan. 12, 2004, now Pat. No. 7,335,231, which is a continuation of application No. 10/057,284, filed on Jan. 24, 2002, now abandoned.

(60) Provisional application No. 60/264,153, filed on Jan. 25, 2001.

(51) Int. Cl.
*A61F 2/42* (2006.01)

(52) U.S. Cl. .................................................. 623/22.15

(58) Field of Classification Search ............... 623/20.12, 623/20.13, 20.24, 21.17, 22.15, 22.18
See application file for complete search history.

(56) References Cited

U.S. PATENT DOCUMENTS

| 3,656,184 | A | * | 4/1972 | Chambers ................. 623/22.15 |
| 4,241,463 | A | | 12/1980 | Khovaylo |
| 4,279,041 | A | | 7/1981 | Buchholz |
| 4,619,658 | A | | 10/1986 | Pappas et al. |
| 4,624,674 | A | | 11/1986 | Pappas et al. |
| 4,676,798 | A | | 6/1987 | Noiles |
| 4,798,610 | A | | 1/1989 | Averill et al. |
| 4,936,855 | A | | 6/1990 | Sherman |
| 4,950,299 | A | | 8/1990 | Noiles |
| 4,960,427 | A | | 10/1990 | Noiles |

(Continued)

FOREIGN PATENT DOCUMENTS

CH          644 511 A      8/1984

(Continued)

OTHER PUBLICATIONS

Anderson, et al. "Constrained Acetabular Components," *The Journal of Arthroplasty*, 9(1):17-23 (1994).

(Continued)

*Primary Examiner* — Bruce E Snow
(74) *Attorney, Agent, or Firm* — Ropes & Gray LLP (57) ABSTRACT

Methods, systems and devices for preventing prosthetic articulating surfaces from separating from each other. A containment system according to one embodiment seeks to prevent an implant stem head from dislocating from a prosthetic component while providing an increased range of motion over conventional constrained components. In one embodiment, an implant structural member includes a cavity and an opening having a lip, including a web along a portion of the lip. An implant stem head has a cooperating surface that corresponds with the web, so that when the cooperating surface of the implant stem head is aligned with the web, the head may be inserted into the implant structural member. The implant stem head is then rotated and the femoral stem component attached, thereby preventing dislocation of the head.

2 Claims, 9 Drawing Sheets

U.S. PATENT DOCUMENTS

| | | | |
|---|---|---|---|
| 5,019,105 A | 5/1991 | Wiley |
| 5,049,158 A | 9/1991 | Engelhardt et al. |
| 5,062,853 A | 11/1991 | Forte |
| 5,133,763 A | 7/1992 | Mullers |
| 5,222,984 A | 6/1993 | Forte |
| 5,226,917 A | 7/1993 | Schyver et al. |
| 5,263,988 A | 11/1993 | Huebner |
| 5,314,487 A | 5/1994 | Schryver |
| 5,314,491 A | 5/1994 | Thongpreda et al. |
| 5,358,532 A | 10/1994 | Evans et al. |
| 5,383,938 A | 1/1995 | Rohr et al. |
| 5,425,778 A | 6/1995 | Zichner et al. |
| 5,458,649 A | 10/1995 | Spotorno et al. |
| 5,507,826 A | 4/1996 | Besselink et al. |
| 5,549,681 A | 8/1996 | Segmuller et al. |
| 5,549,693 A | 8/1996 | Roux et al. |
| 5,676,704 A | 10/1997 | Ries et al. |
| 5,725,587 A | 3/1998 | Garber |
| 5,725,591 A | 3/1998 | DeCarlo, Jr. et al. |
| 5,782,928 A | 7/1998 | Ries et al. |
| 5,800,555 A | 9/1998 | Gray, III |
| 5,824,108 A | 10/1998 | Huebner |
| 5,879,404 A | 3/1999 | Bateman et al. |
| 5,916,270 A | 6/1999 | Lipman |
| 5,931,870 A | 8/1999 | Cuckler et al. |
| 5,935,175 A | 8/1999 | Ostiguy, Jr. et al. |
| 5,964,809 A | 10/1999 | Lin et al. |
| 5,989,293 A | 11/1999 | Cook et al. |
| 6,042,611 A | 3/2000 | Noiles |
| 6,042,612 A | 3/2000 | Voydeville |
| 6,093,208 A | 7/2000 | Tian |
| 6,096,083 A | 8/2000 | Keller et al. |
| 6,099,571 A | 8/2000 | Knapp |
| 6,129,765 A | 10/2000 | Lopez et al. |
| 6,206,929 B1 | 3/2001 | Ochoa et al. |
| 6,610,097 B2 | 8/2003 | Serbousek |
| 6,746,487 B2 | 6/2004 | Scifert et al. |
| 7,335,231 B2 * | 2/2008 | McLean .................... 623/22.15 |
| 7,749,277 B2 * | 7/2010 | McLean .................... 623/22.15 |
| 2002/0116068 A1 | 8/2002 | McLean |
| 2004/0143341 A1 | 7/2004 | McLean |
| 2008/0125866 A1 | 5/2008 | McLean |

FOREIGN PATENT DOCUMENTS

| | | |
|---|---|---|
| DE | 93 12 150 U | 10/1993 |
| DE | 199 26 923 A | 12/2000 |
| DE | 200 11 728 U1 | 1/2001 |
| EP | 0 412 438 A | 2/1991 |
| EP | 0 611 008 A | 8/1994 |
| EP | 0 773 007 | 11/1995 |
| EP | 0 694 294 A | 1/1996 |
| EP | 0 867 158 A | 9/1998 |
| EP | 0 945 109 A | 9/1999 |
| FR | 2 430 221 A | 2/1980 |
| FR | 2 437 199 A | 4/1980 |
| FR | 2 684 544 A | 6/1993 |
| FR | 2 765 100 A | 12/1998 |
| FR | 2 785 524 A | 5/2000 |
| FR | 2 785 525 A | 5/2000 |
| FR | 2 795 302 A | 12/2000 |
| WO | WO 94/05234 | 3/1994 |
| WO | WO 01/76511 A | 10/2001 |
| WO | WO 02/00141 A | 1/2002 |

OTHER PUBLICATIONS

Lombardi, et al., "Preliminary Report on the S-ROM™ Constraining Acetabular Insert: A Retrospective Clinical Experience," *Orthopedics*, 14(3):297-303 (1991).

Brochure entitled "Howmedica Osteonics Constrained Acetabular Insert Surgical Protocol," *Stryker Howmedica Osteoncs*, 11 pages (1999).

Brochure entitled Ringloc® Constrained Liner Technique, *Biomet Inc.*, 6 pages (1998).

Tradonsky, et al., "A comparison of the Disassociation Strength of Modular Acetabular Components," *Clinical Orthopaedics and Related Research*, 296:154-160 (1993).

Rosner, et al., Cup-Liner Conformity of Modular Acetabular Designs, Orthopaedic Research Laboratories, The Mt. Sinai Medical Center, Cleveland, Ohio 44106, six pages (1995).

Goetz, et al., "Salvage of Total Hip Instability with a Constrained Acetabular Component," *Clinical Orthopaedics and Related Research*, 355:171-181 (1998).

Goetz, et al., "Salvage of a Recurrently Dislocating Total Hip Prosthesis with Use of a Constrained Acetabular Component. A Retropective Analysis of Fifty-Six Cases," *Journal of Bone and Joint Surgery*, 80-A(4):502-509 (1998).

Cameron, H., "Use of a Constrained Acetabular Component in Revision Hip Surgery," *Contemporary Orthop.*, 23(5):481-484 (1991).

Fisher, et al., "Constrained Acetabular Cup Disassembly," *Journal Arthrop.*, 9(3):325-329 (1994).

Kaper, B., P. et al., "Failure of a Constrained Acetabular Prosthesis of a Total Hip Arthroplasty," *Journal of Bone and Joint Surgery*, 80-A(4):561-565 (1998).

Schulte, et al., "The outcome of Charnley total hip arthroplasty with cement after a minimum twenty-year followup. The results of one surgeon," *Journal of Bone and Joint Surgery*, 75-A(7):961-975 (1993).

Turner, "Postoperative Total Hip Prosthetic Femoral Head Dislocations. Incidence, Etiologic Factors, and Management," *Clinical Orthopaedics and Related Research*, 301:196-204 (1994).

Paterno, et al., "The influence of patient related factors and the position of the acetabular component on the rate of dislocation after total hip replacement," *Journal of Bone and Joint Surgery*, 79A(8) (1997).

Ali Khan, et al., "Dislocation Following Total Hip Replacement," *Journal of Bone and Joint Surgery*, 214-218 (1981).

Hedlundh, et al. "Influence of Surgical Approach on Dislocations After Charnley Hip Arthroplasty," *Journal of Arthroplasty*, 10(5):609-614 (1995).

Kristiansen, et al., "Dislocation Following Total Hip Arthroplasty," *Arch. Orthop. Trauma Surg.*, 103:375-377 (1985).

Morrey, "Difficult Complications After Hip Joint Replacement Dislocation," *Clinical Orthopaedics and Related Research*, 344:179-187 (1997).

Woo, et al., "Dislocations after Total Hip Arthroplasty," *Journal of Bone and Joint Surgery*, 64-A(9):1295-1306 (1982).

T. Cobb, et al., The Elevated-Rim Acetabular Liner in Total Hip Arthroplasty: Relationship to Postoperative Dislocation, *Journal of Bone and Joint Surgery*, vol. 78-A, No. 1, Jan. 1996, pp. 80-86.

CeraNews Special DUOLOX®-System aus BIOLOX® forte, Feb. 1998, four pages.

Final Office Action for U.S. Appl. No. 10/057,284, mailed Aug. 13, 2003.

International Search Report for PCT/US03/08322, mailed Mar. 18, 2003.

Non-Final Office Action for U.S. Appl. No. 10/057,284, mailed Mar. 26, 2003.

Amendment and Response for U.S. Appl. No. 10/057,284, mailed Jun. 16, 2003.

Office Action for U.S. Appl. No. 10/755,701, mailed Apr. 27, 2006.

Response for U.S. Appl. No. 10/755,701, mailed May 30, 2006.

Non-Final Office Action for U.S. Appl. No. 10/755,701, mailed Jun. 22, 2006.

Response to First Office Action for U.S. Appl. No. 10/755,701, mailed Nov. 15, 2006.

Final Office Action for U.S. Appl. No. 10/755,701, mailed Jan. 30, 2007.

Final Office Action for U.S. Appl. No. 10/755,701, mailed Apr. 9, 2007.

Response to Final Office Action for U.S. Appl. No. 10/755,701, mailed Jun. 11, 2007.

Advisory Action for U.S. Appl. No. 10/755,701, mailed Jul. 6, 2007.

Notice of Allowance for U.S. Appl. No. 10/755,701, mailed Sep. 27, 2007.

Non-Final Office Action for U.S. Appl. No. 12/026,088, mailed Mar. 11, 2009.

Amendment and Response to Non-Final Office Action for U.S. Appl. No. 12/026,088, mailed Jul. 13, 2009.

Final Office Action for U.S. Appl. No. 12/026,088, mailed Nov. 13, 2009.
Response to Final Office Action for U.S. Appl. No. 12/026,088, mailed Feb. 3, 2010.
Notice of Allowance for U.S. Appl. No. 12/026,088, mailed Mar. 1, 2010.

U.S. Appl. No. 12/790,067, filed May 28, 2010.
Office Action for U.S. Appl. No. 12/790,067, mailed Jul. 14, 2010.
International Search Report for PCT/US02/02353.

* cited by examiner

CONTAINMENT SYSTEM FOR CONSTRAINING A PROSTHETIC COMPONENT

RELATED APPLICATIONS

This application is a continuation of U.S. Ser. No. 12/026,088 filed Feb. 5, 2008 entitled "CONTAINMENT SYSTEM FOR CONSTRAINING A PROSTHETIC COMPONENT," now allowed, which is a continuation of U.S. Ser. No. 10/755,701 filed Jan. 12, 2004, which issued on Feb. 26, 2008 as U.S. Pat. No. 7,335,231, which is a continuation of U.S. Ser. No. 10/057,284 filed Jan. 24, 2002, which claims priority to Provisional Application No. 60/264,153, filed Jan. 25, 2001 entitled "Captive Head for Bipolar Endoprosthesis," all of which are herein incorporated by reference.

FIELD OF THE INVENTION

The invention is directed generally to methods, systems and devices related to prosthetic implants, including a device for preventing prosthetic articulating surfaces from separating from each other, and more specifically to a device for preventing an implant stem head from dislocating from an a prosthetic component.

BACKGROUND OF THE INVENTION

Artificial implants, including hip joints, shoulder joints and knee joints, are widely used in orthopedic surgery. Hip joint prostheses are common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic materials. Prosthetic components are generally made from either metals, ceramics, or plastics.

Total hip arthroplasty and hemi-arthroplasty are two procedures well known within the medical industry for replacing all or part of a patient's hip. A total hip arthroplasty replaces both the femoral component and the acetabular surface of the joint, so that both a femoral prosthesis and an acetabular prosthesis are required. A conventional acetabular prosthesis may include a cup, a cup and a liner, or in some cases only a liner, all of which may be formed in various shapes and sizes. Generally, a metal cup and a polymeric liner are used. However, the liner may be made of a variety of materials, including polyethylene, ultra high molecular weight polyethylene and ceramic materials. The cup is usually of generally hemispherical shape and features an outer, convex surface and an inner, concave surface that is adapted to receive a cup liner. The liner fits inside the cup and has a convex and concave surface. The cup liner is the bearing element in the acetabular component assembly. The convex surface of the liner corresponds to the inner concave surface of the cup or acetabulum, and the liner concave surface receives the head of a femoral component. An acetabular cup may include a highly polished inner surface in order to decrease wear.

The liner concave surface, or internal concave surface, is characterized by features relative to an axis through the center of the concave surface. This axis may or may not be aligned with the central axis of the shell. In a typical liner the concave surface has a hemispherical geometry and is also referred to as the internal diameter. In such liners, the geometry is characterized by features that are concentric to an axis that runs through the center of the internal diameter.

An acetabular prosthesis may be fixed in the reamed acetabulum of a patient. Such a prosthesis may include a cup (or a cup and liner assembly) that is fixed either by placing screws through apertures in the cup or by securing the cup with cement. In some cases, only a liner is cemented in a patient due to poor bone stock. In other cases, a cup having a porous surface may be press fit into the reamed acetabular surface.

A femoral prosthesis used in total hip arthroplasty generally includes a spherical or near-spherical head attached to an elongate stem with a neck connecting the head and stem. In use, the elongate stem is located in the intramedullary canal of the femur and the spherical or near-spherical head articulates relative to the acetabular component. Femoral prostheses used in total hip arthroplasty procedures may or may not differ from an endoprosthesis used in a hemi-arthroplasty, described below. However, the femoral head of each type prosthesis is generally a standard size and shape. Various cups, liners, shells, stems and other components may be provided in each type arthroplasty to form modular prostheses to restore function of the hip joint.

Hemi-arthroplasty refers to replacing part of a hip joint, such as replacing a femoral component so that a femoral prosthesis articulates against natural body tissue in the patient's acetabulum. A femoral prosthesis implanted during a hemi-arthroplasty is generally referred to as an endoprosthesis. Generally, an endoprosthesis includes a stem, a head, and may include additional components such as shells and liners. Current endoprosthesis designs include (1) monoblock; (2) two-component; (3) three-component; and (4) five-component designs. A monoblock endoprosthesis is a one-piece structure including a femoral stem and head. Polarity refers to the number of articulating surfaces a prosthesis contains. A monoblock endoprosthesis has one articulation surface between the head and the patient's natural acetabulum, and is therefore referred to as monopolar.

A two-component endoprosthesis includes a femoral component and a shell. The femoral component may include a modular head and stem. A two-component design may be bipolar, so that the head articulates relative to the shell and the shell articulates relative to the acetabulum. A three-component endoprosthesis includes a femoral component, a liner, and a shell. Similar to a two-component design, the femoral component may include a modular head and stem. A three-component endoprosthesis may either be: bipolar, in which the liner is fixed in the shell; or tripolar, in which the head articulates relative to the liner, the liner articulates relative to the shell, and the shell articulates relative to the acetabulum. A five-component endoprosthesis includes a femoral component (which may include a modular head and stem), a first liner, a first shell, a second liner, and a second shell. Both of the first and second liners are fixed inside each of the first and second shells. Therefore, this design is a tripolar design: the second shell is free to articulate with respect to the acetabulum, the modular head of the femoral component articulates with respect to the first liner and the first shell articulates relative to the second liner. Thus, endoprostheses may be described both with respect to the number of components and with respect to the number of articulating surfaces as installed in a patient. Some current designs may also include a mechanical device, such as a snap-ring, for constraining the femoral head, further described below.

Endoprostheses, as well as total hip prostheses, may also be described as constrained and non-constrained prostheses. Non-constrained prostheses rely on the downward force of the body through the joint and the tension created by the soft tissue, including the muscles, ligaments and tendons, to retain the prosthesis in its implanted position. Other prostheses include mechanisms for preventing dislocation of the components, such as the implant stem head. Typically, these prostheses have restraint mechanisms that result in a smaller range of motion of the hip joint, and are generally referred to as "constrained" components.

One example of a restraint mechanism is a shell or liner having greater than hemispherical coverage around the head such that the head is constrained within the internal diameter, thus preventing subluxation and dislocation. In contrast to standard-liners, constrained liners employ an extended, elevated portion over a segment of the periphery of the liner internal diameter in order to increase coverage of the femoral head and thus reduce the likelihood of dislocation and aid in reduction of the head should subluxation occur. While use of a constrained components is generally not desirable due to resulting decreased range of motion, the use of constrained components may be beneficial in cases of tenuous stability in order to avoid dislocation. See e.g. T. Cobb, et al., The Elevated-Rim Acetabular Liner in Total Hip Arthroplasty: Relationship to Postoperative Dislocation, Journal of Bone and Joint Surgery, Vol. 78-A, No. 1, January 1996, pp. 80-86. However, constrained components have a reduction in the arc of motion to contact in the direction of the elevated lip segment, thus, there is a substantial loss of overall range of motion compared to a standard liner. An implant stem head constrained by a shell or liner may dislocate if the femoral component rotates beyond the range of motion permitted by the assembly. Dislocation may occur because the edge or lip of the liner or shell that retains the implant stem head acts as a fulcrum about which the femoral component pivots, thereby causing the implant stem head to dislocate from its position within the liner or shell of the prosthesis. Dislocation of a hip prosthesis is painful and often requires medical intervention.

Three component bipolar endoprostheses including polyethylene liners are known in the industry, and suffer from at least three major clinical problems. First, the vast majority of articulation occurs between the liner and the shell, and it is not uncommon to obtain almost no relative motion between the shell and the acetabulum. Second, there is often a considerable amount of polyethylene wear debris generated from the device due to fatigue loading of the liner. Finally, there is a lower limit to the size of the shell due to the need to incorporate a standard head size and an appropriately thick liner. Current solutions to these problems include a design having a ceramic shell, a ceramic head and a polyethylene snap ring, which locks the head in the shell. Such designs frequently lead to polyethylene wear and have a complex assembly. Another solution has been use of a unipolar monoblock device, which does not require a liner but which results in excessive wear of the acetabulum.

Thus, there exists a need for a prosthetic component capable of retaining an implant stem head to prevent it from dislocating while providing a larger range of motion than is allowed by conventional constrained prostheses. There is also a need for a prosthetic component capable of retaining an implant head to prevent it from dislocating while eliminating the requirement of an inner bearing surface, or liner.

SUMMARY OF THE INVENTION

Set forth below is a brief summary of systems and methods according to the invention that addresses the foregoing problems and provides benefits and advantages in accordance with the purposes of the present invention as embodied and broadly described herein. A prosthesis according to one embodiment of this invention provides a constrained prosthesis with an increased range of motion over current constrained prostheses. According to one embodiment of this invention, a constrained prosthesis prevents dislocation of a femoral component. A prosthesis of this invention may be used with humans and animals and may be used with conventional hip prostheses including endoprostheses and prosthesis used in total hip arthroplasty.

A containment system according to one embodiment of this invention includes an implant structural member having a generally spherical outer surface and having a cavity and opening adapted to receive an implant stem head or other prosthetic component. The opening of the cavity of the implant structural member includes a lip having a web for retaining the implant stem head within the cavity and preventing it from dislocating. The web comprises only a portion of the lip forming the opening As a result, the femoral component is able to travel through a larger range of motion than the range of motion provided a femoral component coupled to a conventional constrained prosthesis. In one embodiment, a portion of an outer surface of the implant stem head is configured to correspond to the web on the shell. An implant stem head according to one embodiment of this invention includes an aperture adapted to receive a femoral stem component.

A containment system according to one embodiment of this invention is assembled by first aligning the surface of the implant stem head configured to correspond to the web of the implant structural member in a first orientation so that it corresponds to the web. The implant stem head is then inserted into the implant structural member and rotated until the head aperture is visible through the opening in the implant structural member. The implant stem head cannot be oriented in the first orientation where the surface of the head corresponds with the web while the femoral stem component is coupled to the implant stem head. Therefore, the implant stem head cannot be removed from the implant structural member unless the femoral stem is first removed. As a result, the femoral component cannot dislocate while positioned within a patient.

One feature of a containment system according to one embodiment of this invention is the elimination of the risk of dislocation of a femoral component.

Another feature of a containment system according to one embodiment of this invention is a constrained prosthetic component providing an increased range of motion.

Yet another feature of a containment system according to one embodiment of this invention is that a containment system is inexpensive to manufacture and includes few parts.

Another feature of a containment system according to one embodiment of this invention is the elimination of the need for a polyethylene liner, allowing the use of a larger head diameter with a resulting increase in range of motion and elimination of the possibility of polyethylene wear.

Yet another feature of a containment system according to one embodiment of this invention is a containment system that is easy to assemble and that requires no additional instruments for assembly.

BRIEF DESCRIPTION OF THE DRAWINGS

The accompanying drawings, which are incorporated in and form a part of the specification, illustrate preferred embodiments of the present invention and, together with the description, disclose the principles of the invention.

DETAILED DESCRIPTION OF THE DRAWINGS

Methods, systems and devices according to this invention seek to provide a containment system for preventing prosthetic articulating surfaces from separating from each other while allowing an increased range of motion over conventional constrained prostheses. One embodiment of a containment system according to this invention seeks to provide a hip prosthetic component for constraining an implant stem head of a femoral component while providing an increased range of motion. Generally, a containment system according to one embodiment of this invention, includes an implant structural member having a cavity and an opening to receive an implant stem head. The opening includes a lip and a web along a portion of the lip. The containment system also includes an implant stem head having a cooperating surface with a shape that corresponds with the shape of the web. The implant stem head is adapted so that it may only be inserted into and removed from the implant structural member when the cooperating surface of the head is aligned with the web.

A containment system according to one embodiment of this invention is assembly by aligning the cooperating surface of the implant stem head with the web of the implant structural member and inserting the implant stem head into the implant structural member. The implant stem head is then rotated and the femoral stem component is attached. The implant stem head can only be removed from the implant structural member if the stem is first removed from the head, allowing the cooperating surface of the implant stem head to be oriented with the web. In this manner, the head is constrained in the implant structural member as long as the stem and head are assembled.

Figure 1:
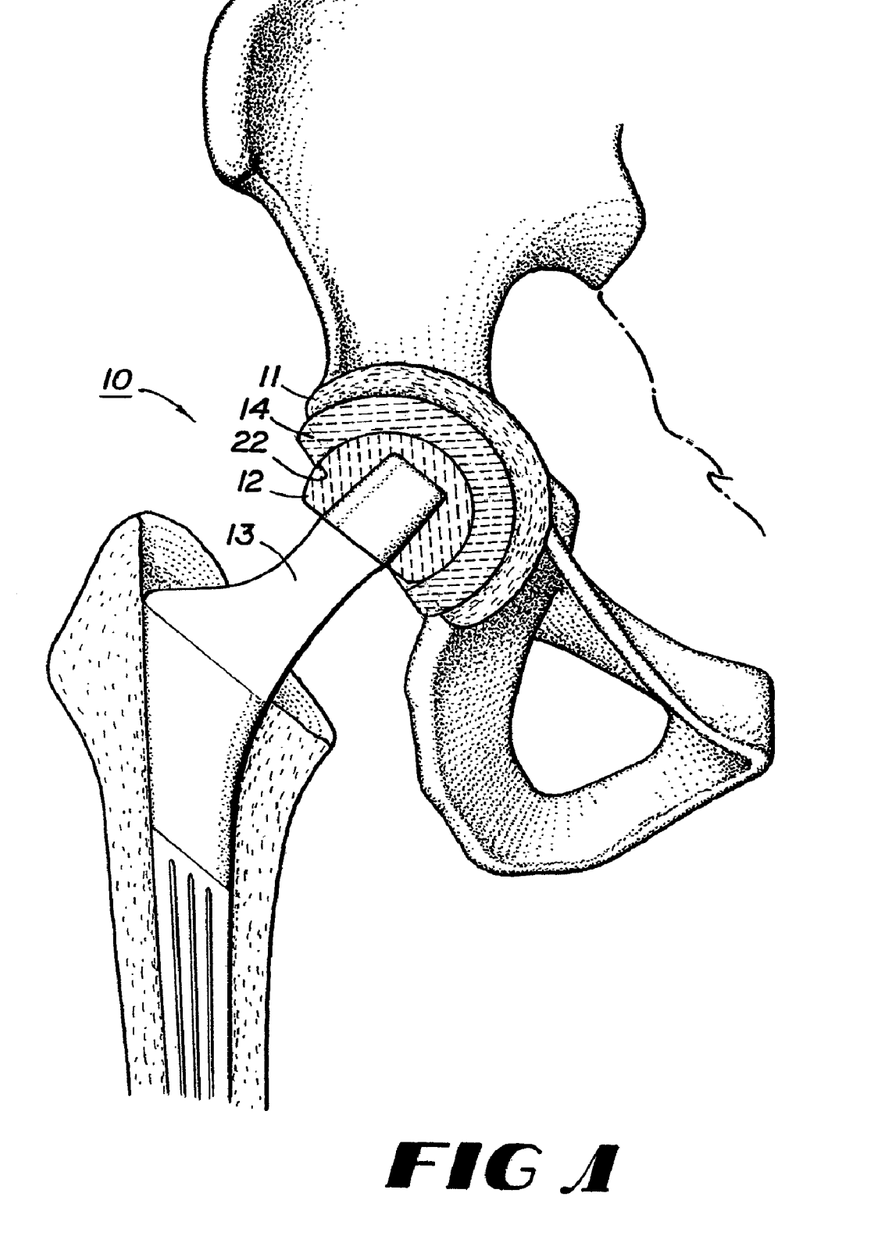
FIG. 1 is a perspective view in cross-section of a containment system according to one embodiment of this invention incorporated within a two-component endoprosthesis.
Figure 2:
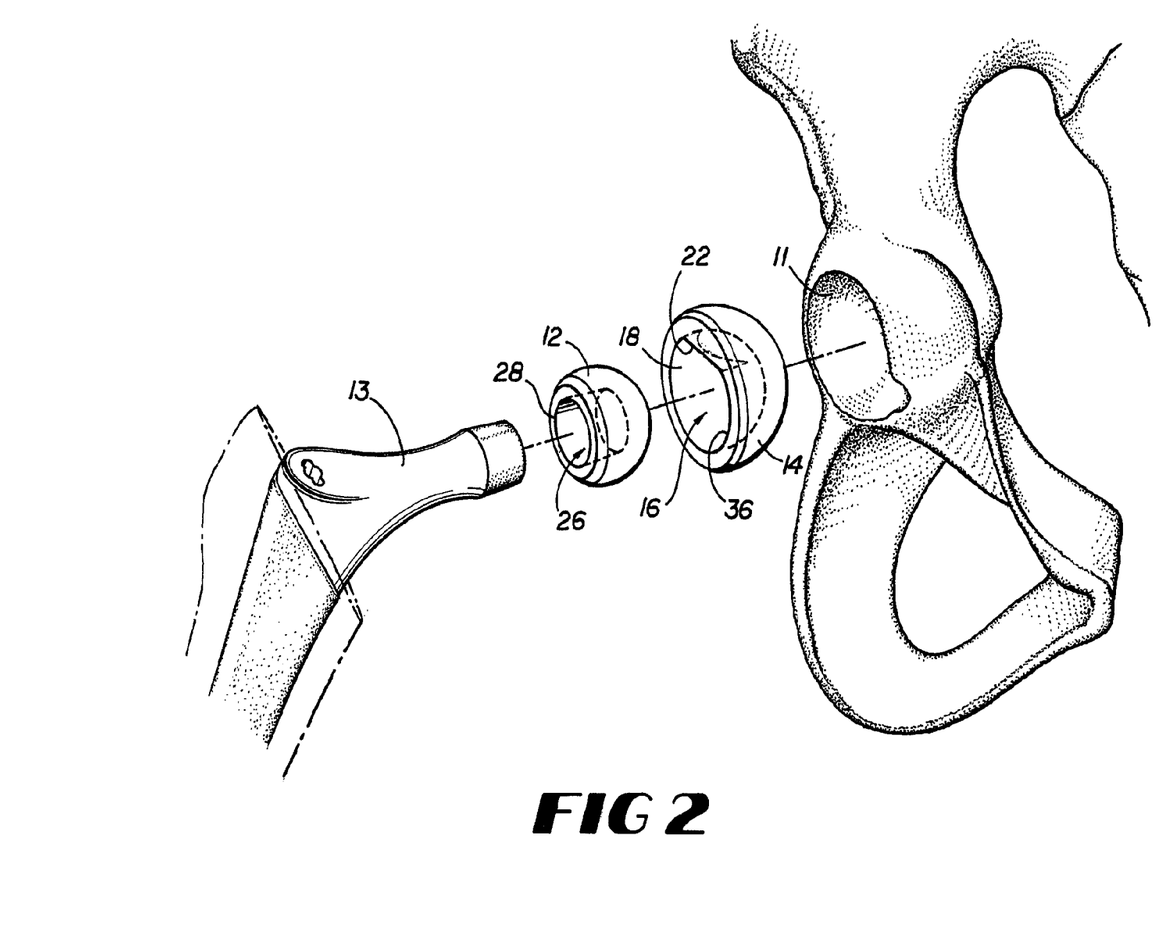
FIG. 2 is an exploded perspective view of the system of FIG. 1.
Figure 3:
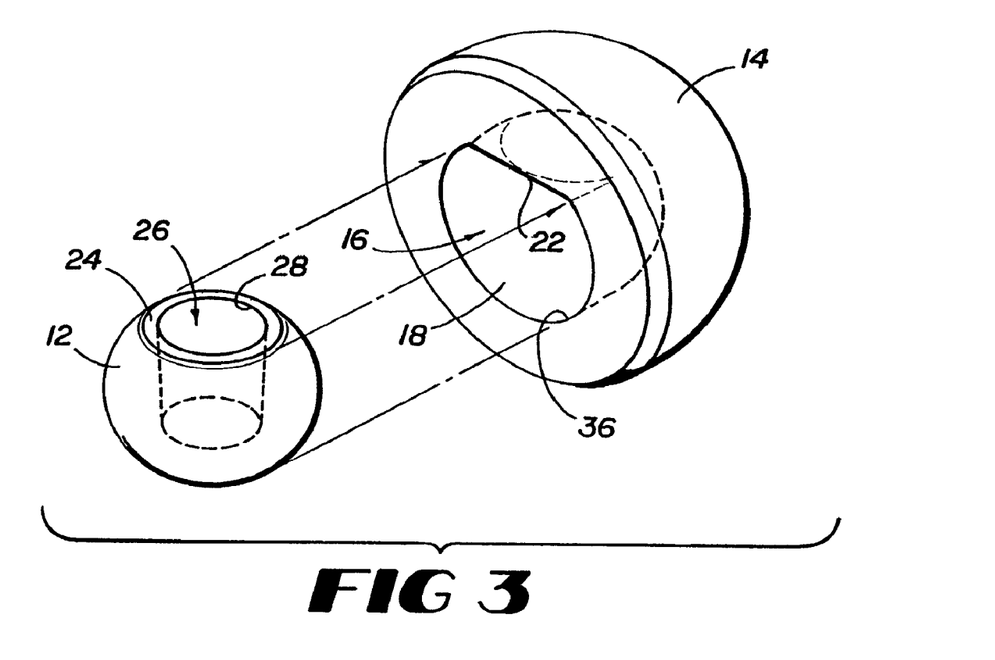
FIG. 3 is an exploded perspective view of an implant structural member and implant stem head of one embodiment of a containment system according to this invention.
Figure 4:
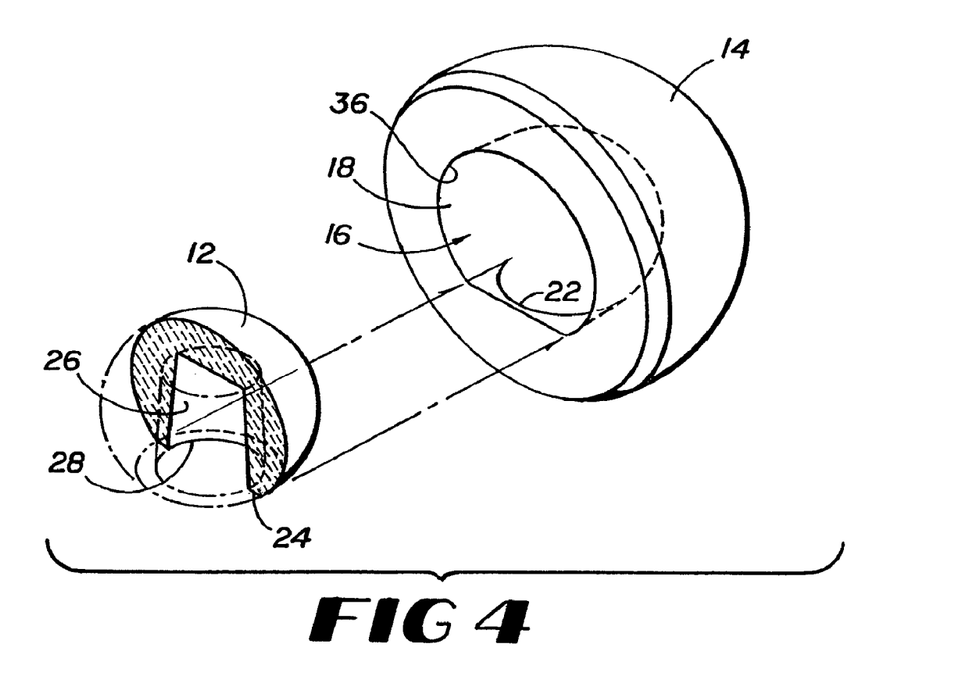
FIG. 4 is an exploded perspective view of the shell and implant stem head of FIG. 3, rotated 180 degrees.
Figure 5:
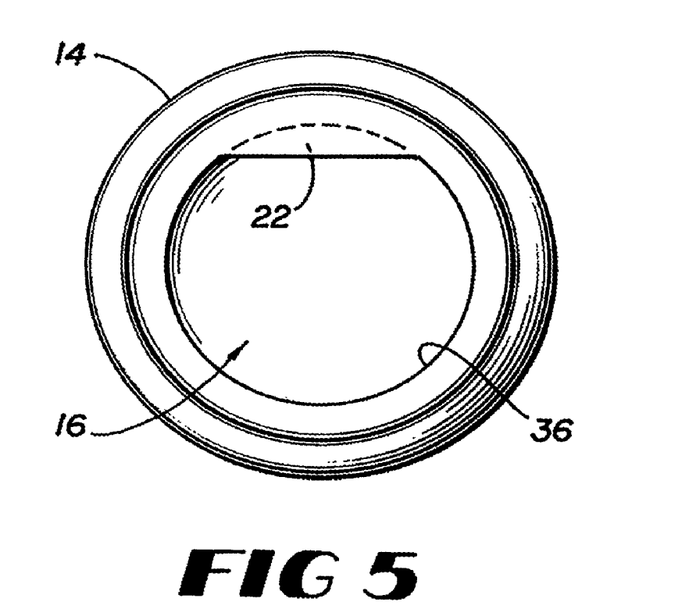
FIG. 5 is a top plan view of the implant structural member of FIG. 1.
Figure 6:
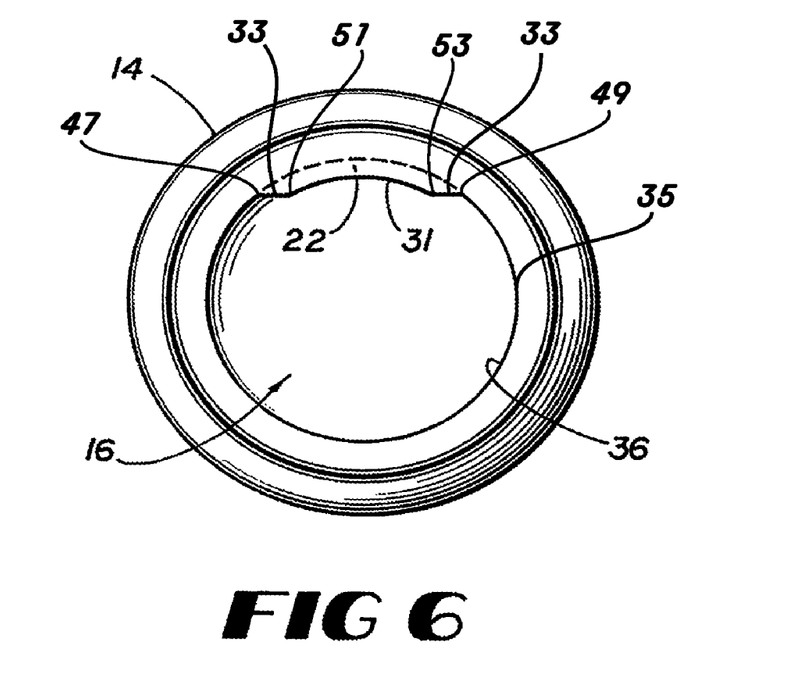
FIG. 6 is a top plan view of an implant structural member according to an alternative embodiment of this invention.

Consider one example of systems and devices according to this invention. Containment system 10 is illustrated as a two-component bipolar endoprosthesis in FIGS. 1 and 2. This containment system 10 includes an implant structural member 14, such as a shell, adapted to receive implant stem head 12, which is adapted to be coupled to femoral stem component 13, the implant stem head and femoral stem component forming a femoral component when assembled. As shown in FIGS. 1 and 2, implant structural member 14 is adapted to fit within acetabulum 11 and is adapted to capture and retain implant stem head 12. Implant structural member 14 includes a cavity 16 that has a generally spherical shape and that is formed by an inner surface 18 and an opening 20 having a substantially arcuate portion 35. Opening 20 includes lip 36 having web 22, which reduces the size of opening 20 so that opening 20 forms a D-shape, as shown in FIG. 5. In an alternative embodiment, shown in FIG. 6, opening 20 is generally D-shaped but web 22 includes curved or substantially arcuate portion 31 (also referred to as a widening portion), which slightly widens the opening 20 and thereby allows the femoral stem component to rotate through a slightly larger range of motion. In this way, opening 20 forms a D-shape having a curved recess that corresponds to arcuate portion 31. Arcuate portion 35 extends along a first path and has a first end 47 and a second end 49, while arcuate portion 31 extends along a second path that is not continuous with the first path and has a third end 51 and a fourth end 53. Connecting or narrowing portions 33 (which in some embodiments can be generally straight) extend along third and fourth paths, respectively. One of the connecting portions 33 connects the first end 47 of the arcuate portion 35 to the third end 51 of the arcuate portion 31 and the other of the connecting portions 33 connects the second end 49 of the arcuate portion 35 to the fourth end 53 of the arcuate portion 31. As illustrated in FIG. 6, arcuate portion 35 is defined as a portion of a first circle, and arcuate portion 31 is defined as a portion of a second circle that is concentric with the first circle and radially offset from the first circle. Neither of connecting portions 33 extend along either the first circle or the second circle. In other embodiments, web 22 has other suitable shapes.

Implant stem head 12 may or may not extend beyond opening 20 of implant structural member 14. For example, as shown in FIGS. 1-2 and 10-11, implant stem head 12 extends beyond opening 20 of implant structural member 14, but head 12 and member 14 may also be adapted so that head 12 does not extend beyond the opening 20. For example, as shown in FIGS. 3-4 and 7-9, implant structural member 14 is adapted to receive implant stem head 12 such that head 12 does not extend beyond opening 20 of implant structural member 14, but may also be adapted so that head 12 does extend beyond the opening 20. In one embodiment, the plane of web 22 is at a right angle to the lip 36; however, in an alternative embodiment, the plane of web 22 is at any suitable angle relative to the lip. The description of the two component containment system 10 is generally applicable to all embodiments shown in FIGS. 1-11, with the only difference being the positioning of the implant stem head relative to the implant structural member, as described above.

Figures 7, 8:
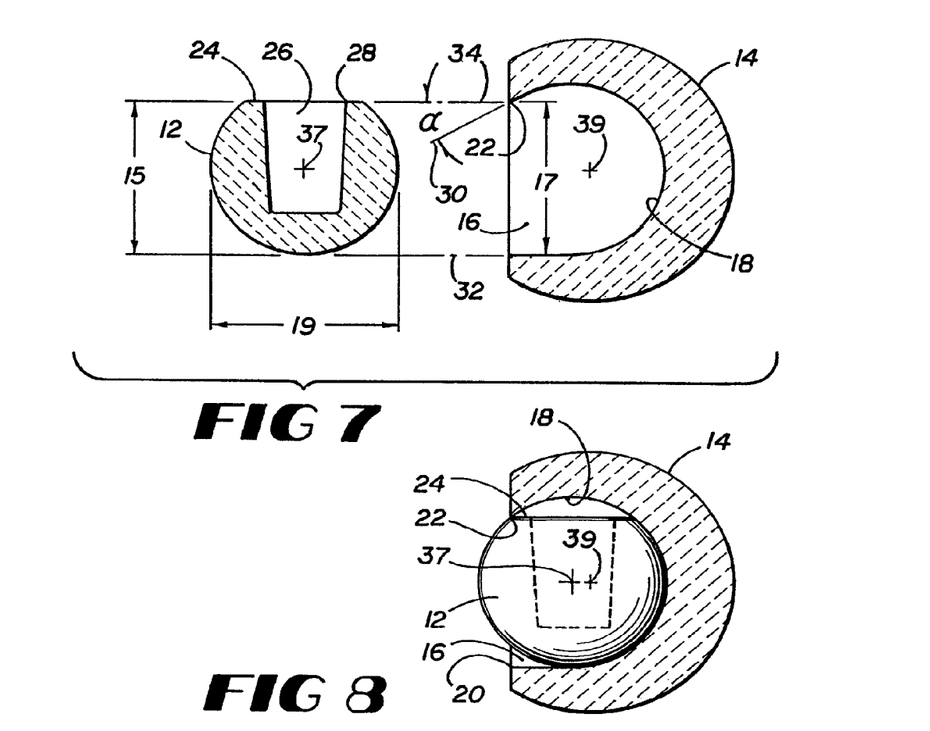
FIG. 7 is a side elevation view in cross-section of the implant structural member and implant stem head of FIG. 3.
FIG. 8 is a side elevation view in cross-section of the implant structural member and implant stem head of FIG. 7, as assembled.

As shown in FIG. 7, first tangent line 30 and second tangent line 32 are not parallel. Instead, first tangent line 30 is at an angle α that is less than 90 degrees relative to reference line 34, which is parallel to second tangent line 32. Web 22 is formed as a continuation of inner surface 18 and maintains the same radius of curvature as other portions of inner surface 18. Thus, web 22 is formed by extending inner surface 18 beyond reference line 34 to form angle α, as shown in FIG. 7. In this configuration web 22 decreases the diameter across opening 20 and does not create a surface likely to cause unnecessary wear on implant stem head 12.

Implant stem head 12 is generally spherical in shape and includes a cooperating surface 24 that enables implant stem head 12 to be inserted within cavity 16 of implant structural member 14. Surface 24 may be flat, as shown in FIGS. 1-4, or may be formed of alternative shapes that correspond to the shape of the web. As shown in FIG. 7, cooperating surface 24 is positioned on implant stem head 12 so that a diameter 15 of implant stem head 12 taken perpendicular to cooperating surface 24 and traveling through the center of implant stem head 12 is slightly smaller than distance 17 within opening 20. This configuration allows implant stem head 12 to be inserted into cavity 16 by aligning cooperating surface 24 with web 22. Orienting cooperating surface 24 in this manner allows implant stem head 12 to be inserted into cavity 16 past web 22, as shown in FIG. 8.

Figure 9:
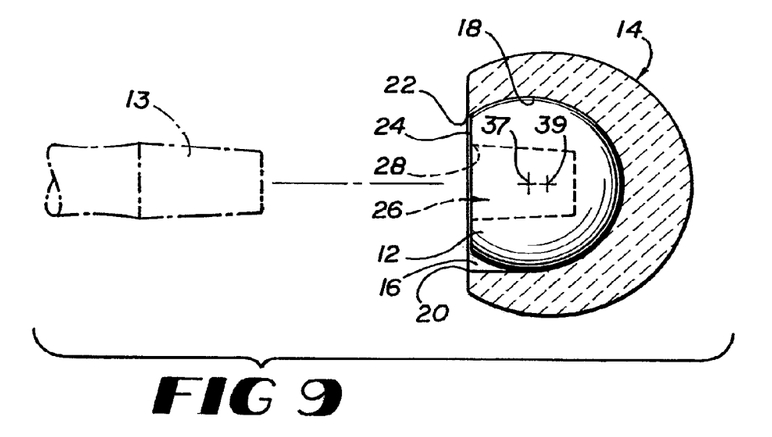
FIG. 9 is a side elevation view in cross-section of the implant stem head and shell of FIG. 8 after the head has been rotated to receive a stem.

After implant stem head 12 has been completely inserted into cavity 16 of implant structural member 14, head 12 is rotated so that head 12 is retained in cavity 16. Specifically, after implant stem head 12 is rotated, head 12 cannot be removed from implant structural member 14 because the diameter 19 of implant stem head 12, shown in FIG. 7, is greater than distance 17 of opening 20, and cooperating surface 24 is no longer oriented to correspond with web 22, as shown in FIG. 9. A femoral stem component 13 is then coupled to head 12, preventing alignment of cooperating surface 24 with web 22 so that head 12 is retained in implant structural member 14. Once femoral stem component 13 has been coupled with head 12, head 12 cannot be removed from shell 14 until femoral stem component 13 has been removed because stem 13 prevents head 12 from being rotated so that cooperating surface 24 aligns with web 22.

As shown in FIGS. 7-9, implant stem head 12 includes cavity 26, which is adapted to receive femoral stem component 13 and which is generally cylindrical. In an alternative embodiment, cavity 26 may be conical, cubical, or any other suitable shape. In other alternative embodiments, cavity 26 may include threads, barbs, rings or any other suitable mechanical connectors to couple head 12 to stem 13. In yet another embodiment, adhesive or cement may be used to couple head 12 to femoral stem component 13.

Figure 10:
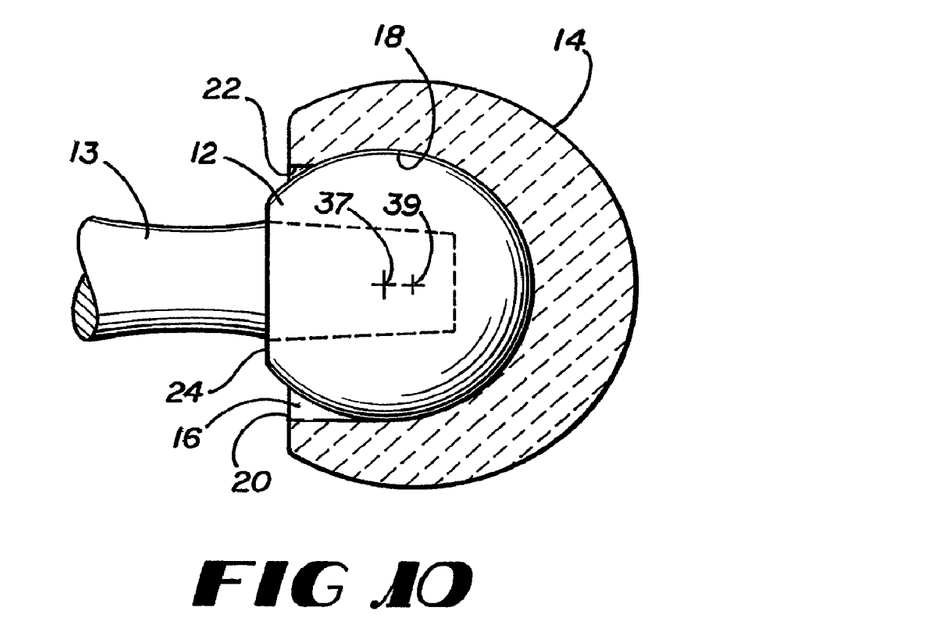
FIG. 10 is a side elevation view in cross-section of the implant stem head, shell and stem of FIG. 1, as assembled.
Figure 11:
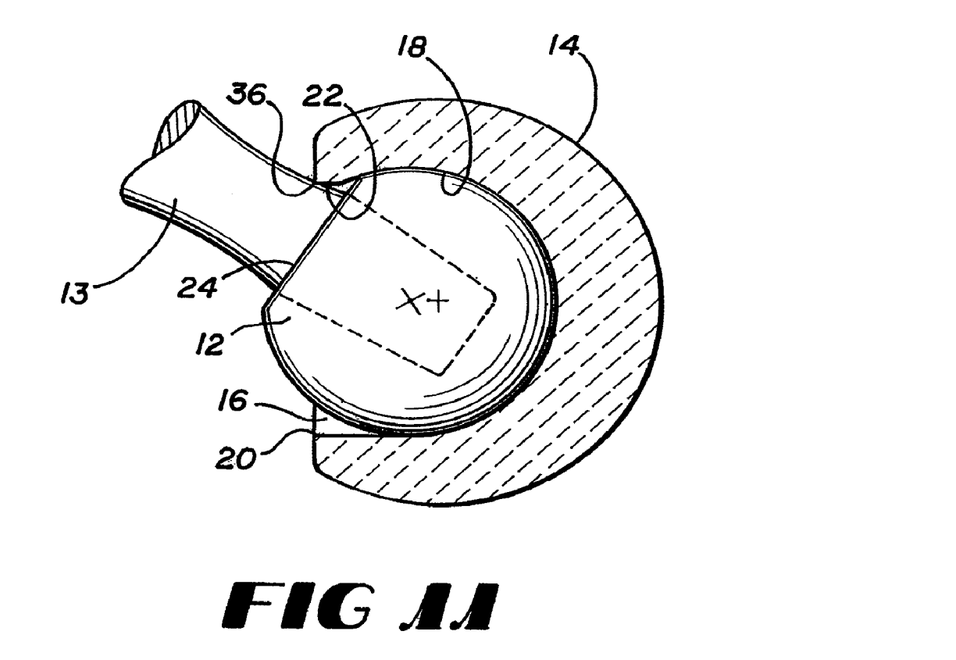
FIG. 11 is a side elevation view in cross-section of the implant stem head, shell and stem of FIG. 1, as assembled and rotated.

In one embodiment, opening 28 of cavity 26 of implant stem head 12 is positioned on cooperating surface 24. In this embodiment, opening 28 is positioned to receive stem 13 only after implant stem head 12 has been rotated to expose opening 28, as shown in FIG. 9. Attachment of stem 13 to implant stem head 12 prevents implant stem head 12 from being rotated so that implant stem head 12 can be removed from cavity 16, as shown in FIG. 10. Specifically, after implant stem head 12 has been attached to stem 13, stem 13 contacts the lip 36 of opening 20 and prohibits implant stem head 12 from being rotated any further, as shown in FIG. 11. Thus, lip 36 of opening 20 defines the range of motion of femoral stem component 13. In another embodiment, opening 28 is positioned within head 12 at a location other than within surface 24. For instance, opening 28 may be located adjacent to surface 24 or in another location on head 12. During use, web 22 is preferably positioned superiorly, as shown in FIG. 2, in order to maximize range of motion and minimize the possibility of subluxation.

In one embodiment according to this invention, off-axis eccentricity is provided. In one embodiment, negative eccentricity is provided, forcing rotation of the implant structural member relative to the acetabulum. In another embodiment, positive eccentricity is provided, resulting in an increased range of motion of the femoral component. For example, as shown in FIGS. 7-9, the center of rotation 37 of implant stem head 12 is not positioned in the same location as the center of shell 39. Center of rotation 37 of implant stem head 12 is positioned closer to opening 20 than the center of shell 39. As a result, the femoral component is less restricted than if both center of rotation 37 and the center of shell 39 were located in the same position.

In one embodiment of this invention, implant stem head 12 is ceramic and implant structural member 14 is a ceramic shell. This embodiment does not include polyethylene in any form, reducing wear debris. In one embodiment, implant stem head 12 is larger than a conventional head, allowing an increased range of motion resulting from the increased diameter of the assembly. In one embodiment, the throat diameter of the shell is reduced to slightly less than a complete hemisphere, further increasing range of motion.

Figure 12:
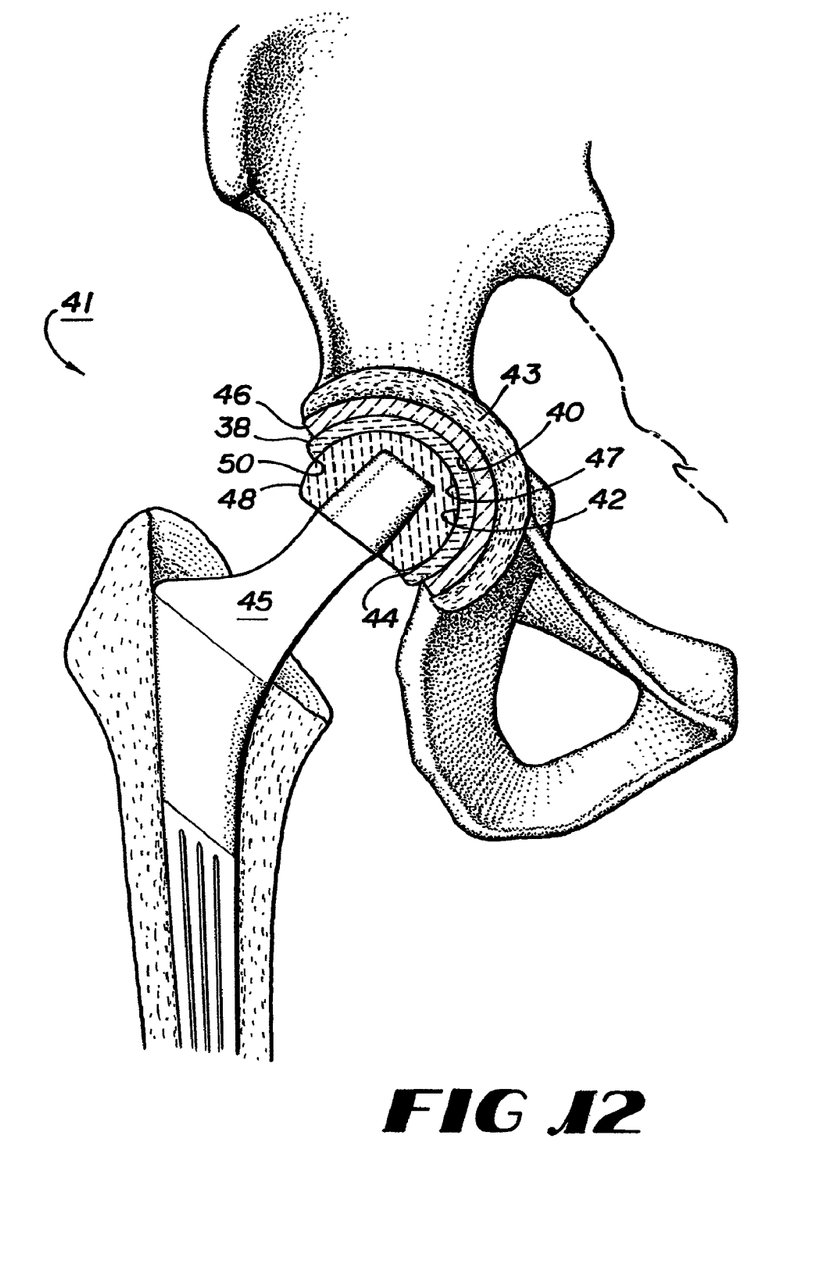
FIG. 12 is a perspective view in cross-section of a containment system according to one embodiment of this invention incorporated within a three-component endoprosthesis.

An alternative embodiment of a containment system according to this invention is illustrated as a three-component tripolar endoprosthesis in FIG. 12. Containment system 41 is very similar to the two-component embodiment described above, with the retention mechanism located within liner 38. For example, containment system 41 includes a shell 46 having a cavity 40 for receiving liner 38. Shell 46 is adapted to be received in acetabulum 43. Liner 38 is adapted to be received in cavity 40 of shell 46 and includes a cavity 47 adapted to receive implant stem head 48. Cavity 47 of liner 38 is defined by an inner surface 42 and opening 44. Inner surface 42 can be formed from any conventional process. As described in the two-component endoprosthesis embodiment above, a web 50 on the lip of liner 38 is positioned to capture an implant stem head 48 and to prevent dislocation of implant stem head 48 while the stem 45 is coupled to head 48.

Figure 13:
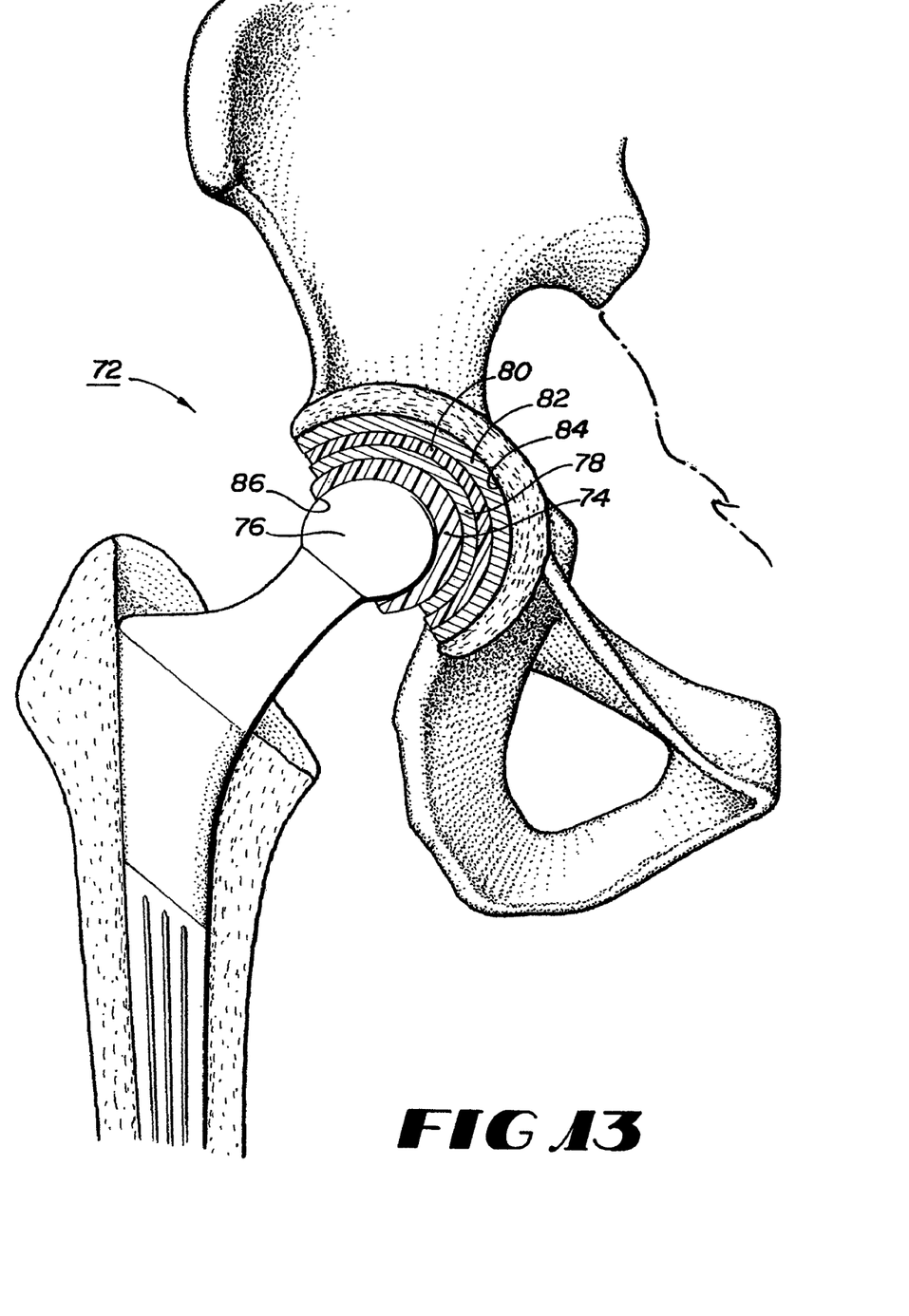
FIG. 13 is a perspective view in cross-section of a containment system according to one embodiment of this invention incorporated within a five-component endoprosthesis.

Yet another alternative embodiment of a containment system according to this invention is illustrated as a five-component endoprosthesis in FIG. 13. Similar to the embodiment of FIG. 12, the retention mechanism of containment system 72 is located on first liner 74, which is adapted to receive implant stem head 76. First shell 78 is adapted to receive first liner 74, while second liner 80 is adapted to receive first shell 78. Second liner 80 is received in second shell 82, which is received in acetabulum 84. First liner 74 includes a web 86 and captures and retains head 76 as described in the embodiments above.

Figure 14:
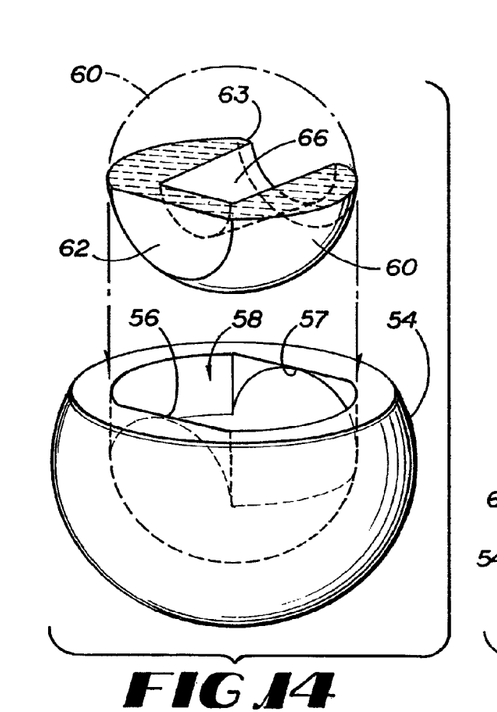
FIG. 14 is an exploded perspective view of a containment system according to an alternative embodiment of this invention.
Figure 15:
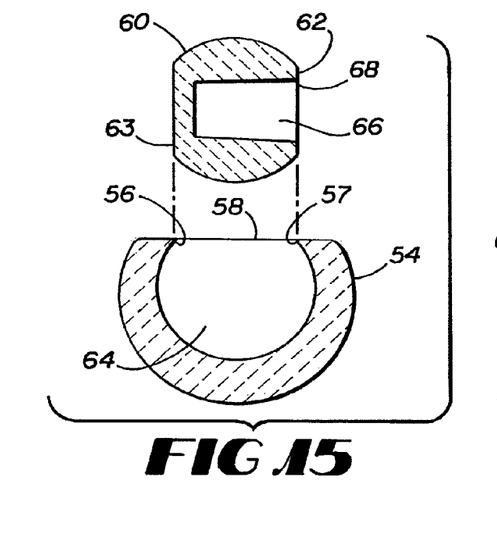
FIG. 15 is a side elevation view in cross-section of the shell and implant stem head of FIG. 14.
Figure 16:
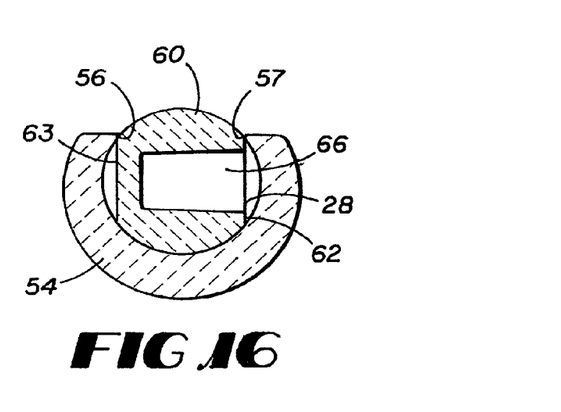
FIG. 16 is a side elevation view in cross-section of the shell and implant stem head of FIG. 14, as assembled.
Figure 17:
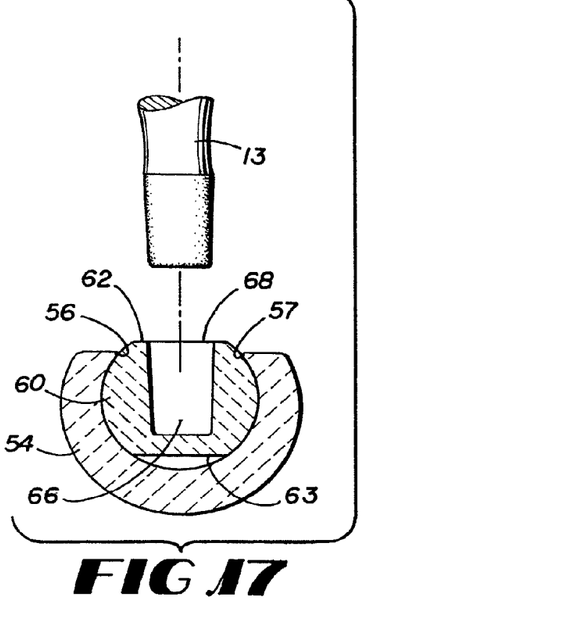
FIG. 17 is a side elevation view in cross-section of the shell and implant stem head of FIG. 14, as assembled and rotated.

In an alternative embodiment, shown in FIGS. 14-17, a containment system includes shell 54 having two webs 56, 57, each positioned on opposing sides of opening 58 of shell 54. Implant stem head 60 includes two cooperating surfaces 62, 63 that correspond with webs 56, 57 so that implant stem head 60 may be inserted into cavity 64 of shell 54. In this embodiment, the containment system functions in the same manner as the embodiments having a single web. For example, implant stem head 60 is positioned so that surfaces 62, 63 correspond with webs 56, 57 as shown in FIGS. 14 and 15. Implant stem head 60 is then inserted into shell 54, as shown in FIG. 16. Implant stem head 60 is then rotated until cavity 66 of head 60 is capable of receiving a femoral stem component 70 through opening 68, as shown in FIG. 17. Other alternative embodiments of a containment system according to this invention may include shells or liners having any appropriate number of webs that may be configured as shown or in alternative configurations, such as three, four or five webs and having heads corresponding to the webs.

The components of the various prostheses described may be made from metal, such as stainless steel and titanium, ceramic, plastic, such as polyethylene, or any other suitable material. In one embodiment, all of the components of a two-component bipolar endoprosthesis are metal. In an alternative embodiment, all of the components of a two-component bipolar endoprosthesis are ceramic. In another embodiment, the shell and implant stem head of a three-component endoprosthesis are either metal or ceramic, while the liner is polyethylene.

The embodiments of a containment system as described above all relate to endoprostheses used in hemi-arthroplasty. Similar embodiments of a containment system according to this invention may be incorporated into a prosthesis used in total hip arthroplasty, using a web to constrain a femoral head component. Alternative embodiments of a containment system according to this invention may be utilized to capture and retain other prosthetic components. For example, a web may be incorporated into a second liner of a five component endoprosthesis in order to capture and retain the first shell and first liner assembly. Additionally, embodiments of a containment system according to this invention may also be used to capture components of other orthopedic prostheses, such as shoulder prostheses and small finger joint prosthesis. For example, a constrained shoulder prosthesis may include a web to capture and retain the humeral head.

One method of using one form of structure according to this invention is as follows. Implant stem head 12, shown in FIG. 7, is positioned to be inserted into shell 14 by orienting implant stem head 12 in a first orientation so that cooperating surface 24 corresponds with web 22. As shown in FIG. 8, implant stem head 12 is inserted into shell 14 so that the outside surface of implant stem head 12 contacts inside surface 18 of shell 14. Implant stem head 12 is then placed in a second orientation by rotating head 12 so that cavity 26 is exposed and in position to receive femoral stem component 13. After femoral stem component 13 has been coupled to implant stem head 12, head 12 cannot be removed from shell 14 unless stem 13 is first removed because stem 13 prevents head 12 from being oriented in a first orientation where cooperating surface 24 corresponds with web 22. The endoprosthesis is then surgically implanted, so that the stem of the femoral component is implanted into the femur of a patient. The endoprosthesis is then implanted in the acetabulum of a pelvis.

The foregoing is provided for purposes of illustrating, explaining, and describing embodiments of this invention. Modifications and adaptations to these embodiments will be apparent to those skilled in the art and may be made without departing from the scope or spirit of this invention or the following claims.

The invention claimed is:

1. A containment system comprising:
   (a) a first implant structural member comprising:
      an outer surface;
      an inner surface defining a cavity;
      a lip comprising an inner edge defining a cavity opening, wherein the inner edge comprises:
         a first substantially arcuate portion having a first end and a second end, wherein the first substantially arcuate portion is defined as a portion of a first circle,
         a second substantially arcuate portion having a third end and a fourth end, wherein the second substantially arcuate portion is defined as a portion of a second circle that is concentric with the first circle and radially offset from the first circle, and
         a first connecting portion and a second connecting portion,
         wherein the first connecting portion connects the first end of the first substantially arcuate portion to the third end of the second substantially arcuate portion, the second connecting portion connects the second end of the first substantially arcuate portion to the fourth end of the second substantially arcuate portion, and neither the first connecting portion nor the second connecting portion extends along either the first circle or the second circle, and
   (b) an implant stem head, the implant stem head comprising:
      a generally spherical body having a surface configured to correspond to at least the first connecting portion enabling the implant stem head to be inserted into the first implant structural member when the implant stem head is in a first orientation; and
      a cavity; and
   (c) a separate femoral stem component which may be inserted into the cavity of the implant stem head,
   wherein the outer surface of the first implant structural member may be received by a shell, and
   wherein the implant stem head may be received by the first implant structural member, and
   wherein after the implant stem head is inserted into the cavity of the first implant structural member, rotated within the first implant structural member, and the femoral stem component inserted into the cavity of the implant stem head, the inner edge locks the implant stem head such that the implant stem head may articulate within the first implant structural member but cannot be removed from the first implant structural member.

2. The containment system of claim 1, wherein the surface of the generally spherical body corresponds to the first connecting portion and to the second connecting portion.

* * * * *